United States Patent [19]
Young et al.

[11] Patent Number: 5,354,132
[45] Date of Patent: * Oct. 11, 1994

[54] FLUID CONTAINMENT BAG

[75] Inventors: Ruth E. Young; Daniel L. Young, both of Escondido; Richard E. Warrick, Encinitas; Clarence A. Cassidy, Carlsbad, all of Calif.

[73] Assignee: American Innotek, Inc., San Marcos, Calif.

[*] Notice: The portion of the term of this patent subsequent to May 26, 2009 has been disclaimed.

[21] Appl. No.: 865,454

[22] Filed: Apr. 9, 1992

Related U.S. Application Data

[60] Division of Ser. No. 657,354, Feb. 15, 1991, Pat. No. 5,116,139, and a continuation-in-part of Ser. No. 404,734, Sep. 8, 1989, abandoned, which is a continuation-in-part of Ser. No. 3,848, Jan. 14, 1987, abandoned.

[51] Int. Cl.$^5$ ............................................. B65D 30/24
[52] U.S. Cl. ........................................ 383/49; 383/10; 383/33; 383/35; 383/36; 383/44; 383/61; 383/63; 383/65; 383/69; 4/144.2; 604/328
[58] Field of Search ................... 383/9, 10, 33, 34, 35, 383/36, 44, 46, 47, 48, 49, 61, 63, 64, 65, 68, 69; 4/144.1, 144.2; 604/327, 328, 329, 323

[56] References Cited

U.S. PATENT DOCUMENTS

| | | |
|---|---|---|
| 1,123,951 | 1/1915 | Swanson . |
| 1,458,640 | 6/1923 | Chase . |
| 2,343,678 | 3/1944 | Larkin . |
| 2,640,484 | 6/1953 | Johnson ............................ 383/44 X |
| 2,883,985 | 4/1959 | Evans ................................. 604/327 |
| 3,297,152 | 1/1967 | Corella et al. . |
| 3,331,421 | 7/1967 | Lambert ............................ 383/44 X |

(List continued on next page.)

FOREIGN PATENT DOCUMENTS

| | | |
|---|---|---|
| 0263315 | 4/1988 | European Pat. Off. . |
| 1815038 | 7/1969 | Fed. Rep. of Germany . |
| 2936622 | 3/1981 | Fed. Rep. of Germany ....... 4/144.2 |
| 2016929 | 9/1979 | United Kingdom . |
| 2094265 | 9/1982 | United Kingdom . |
| 2227728 | 8/1990 | United Kingdom . |

OTHER PUBLICATIONS

Elias, *Mega Molecules* (1985) pp. 155–163.
"Sporty's" Catalogue (1989) p. 65.
"Introducing Restop" brochure (1985)—4 pages.
Hoechst Celanse, "SANWET Superabsorbent Polymers" (date unknown), 5 pages.
Sunrise Medical, "No More Dirty Work" (1989) 4 pages.

*Primary Examiner*—Allan N. Shoap
*Assistant Examiner*—Jes F. Pascua, Jr.
*Attorney, Agent, or Firm*—Brown, Martin, Haller & McClain

[57] ABSTRACT

A containment and disposal bag for human bodily fluids is disclosed which includes a bag having a hollow interior and a top at least partially open to receive the bodily fluids; preferably a funnel structure within the bag to channel said bodily fluids into the interior and to restrict expulsion of bodily fluids from the interior prior to sequestration; a hydrophilic material within the bag which is rapidly gellable upon contact with the bodily fluids in the bag, the gellation serving to essentially completely sequester the bodily fluids and prevent it from thereafter being expelled from the bag; and a closure to close the top of the bag after introduction of the bodily fluids into the bag. The hydrophilic material is commonly a polymer which is activated upon contact with the water-based bodily fluids and which gels rapidly (normally within thirty seconds or less) to sequester the bodily fluids. The hydrophilic material commonly is part of a mixture of materials which also may contain enzymes, deodorants, fragrances, human body abnormality indicators and/or pregnancy indicators. The bag may be rectangular or otherwise shaped to accommodate the user's needs, or may be adapted to be worn by the user. The rapid and complete sequestration of the bodily fluids permits the bag to be easily and conveniently used in a variety of circumstances with minimal possibility that the bodily fluids will become spilled or otherwise expelled from the bag.

49 Claims, 3 Drawing Sheets

U.S. PATENT DOCUMENTS

| | | |
|---|---|---|
| 3,346,883 | 10/1967 | Ersek . |
| 3,366,116 | 1/1968 | Huck . |
| 3,403,410 | 10/1968 | Benzel et al. . |
| 3,403,715 | 10/1968 | Trudel . |
| 3,547,123 | 12/1970 | Sachs . |
| 3,556,102 | 1/1971 | Davis . |
| 3,577,989 | 5/1971 | Anderson . |
| 3,597,770 | 8/1971 | Jacuzzi et al. . |
| 3,612,133 | 10/1971 | Jarund . |
| 3,797,734 | 3/1974 | Fleury et al. . |
| 3,920,179 | 11/1975 | Hall . |
| 4,179,367 | 12/1979 | Barthell et al. . |
| 4,305,161 | 12/1981 | Diaz . |
| 4,387,713 | 6/1983 | Calanni . |
| 4,541,117 | 9/1985 | Ashbeck . |
| 4,581,763 | 4/1986 | Olsen . |
| 5,067,821 | 11/1991 | Young ............................... 383/44 X |
| 5,116,139 | 5/1992 | Young et al. ......................... 383/49 |

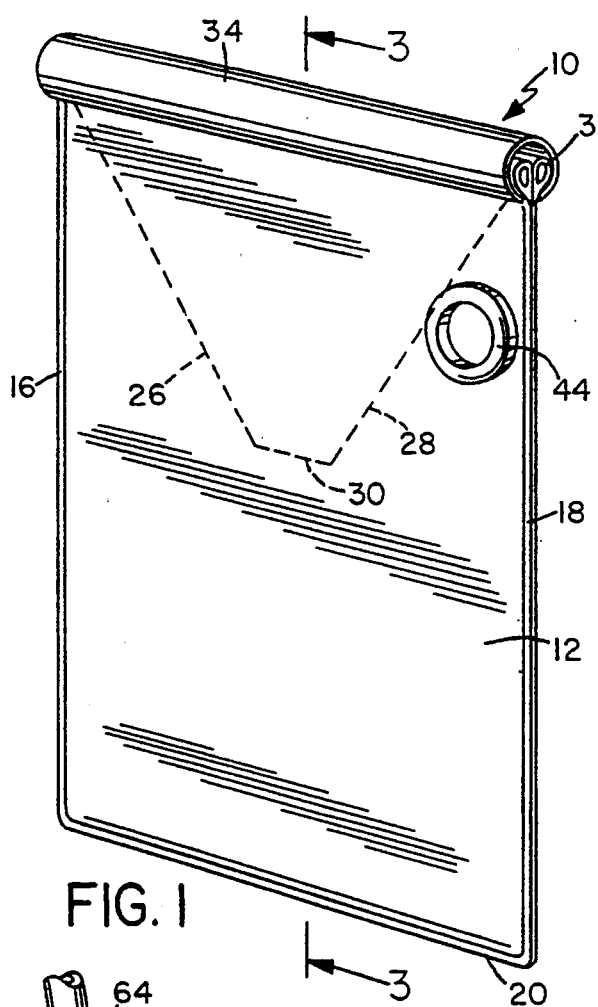
FIG. 1
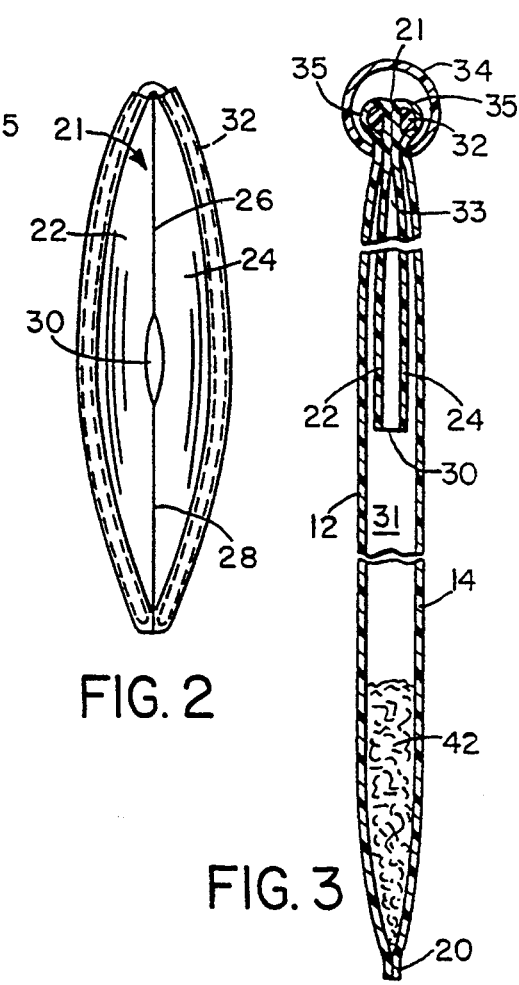
FIG. 2
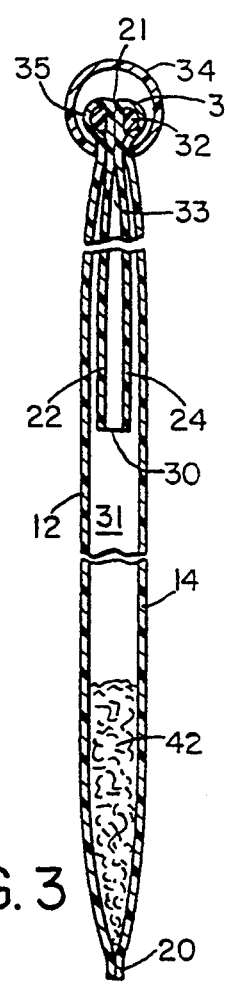
FIG. 3
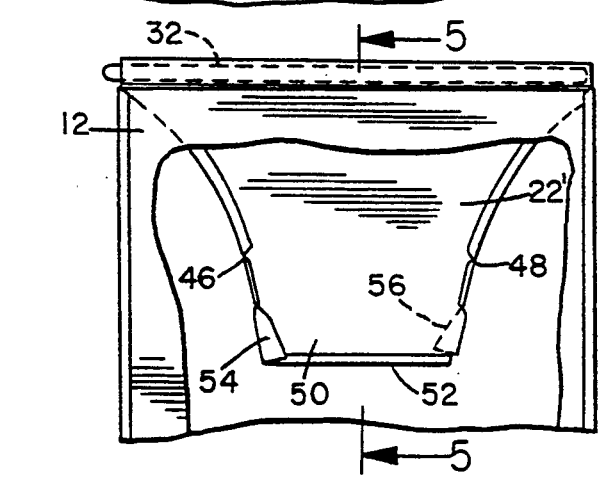
FIG. 4
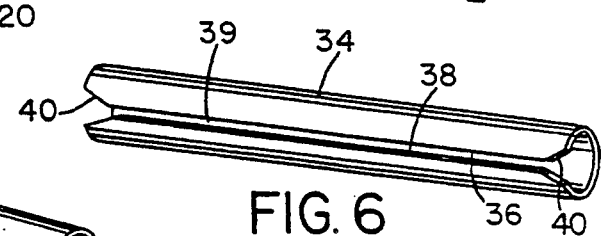
FIG. 6
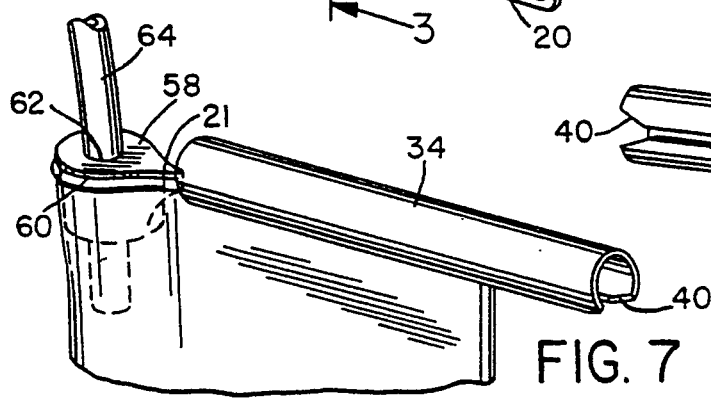
FIG. 7
FIG. 5

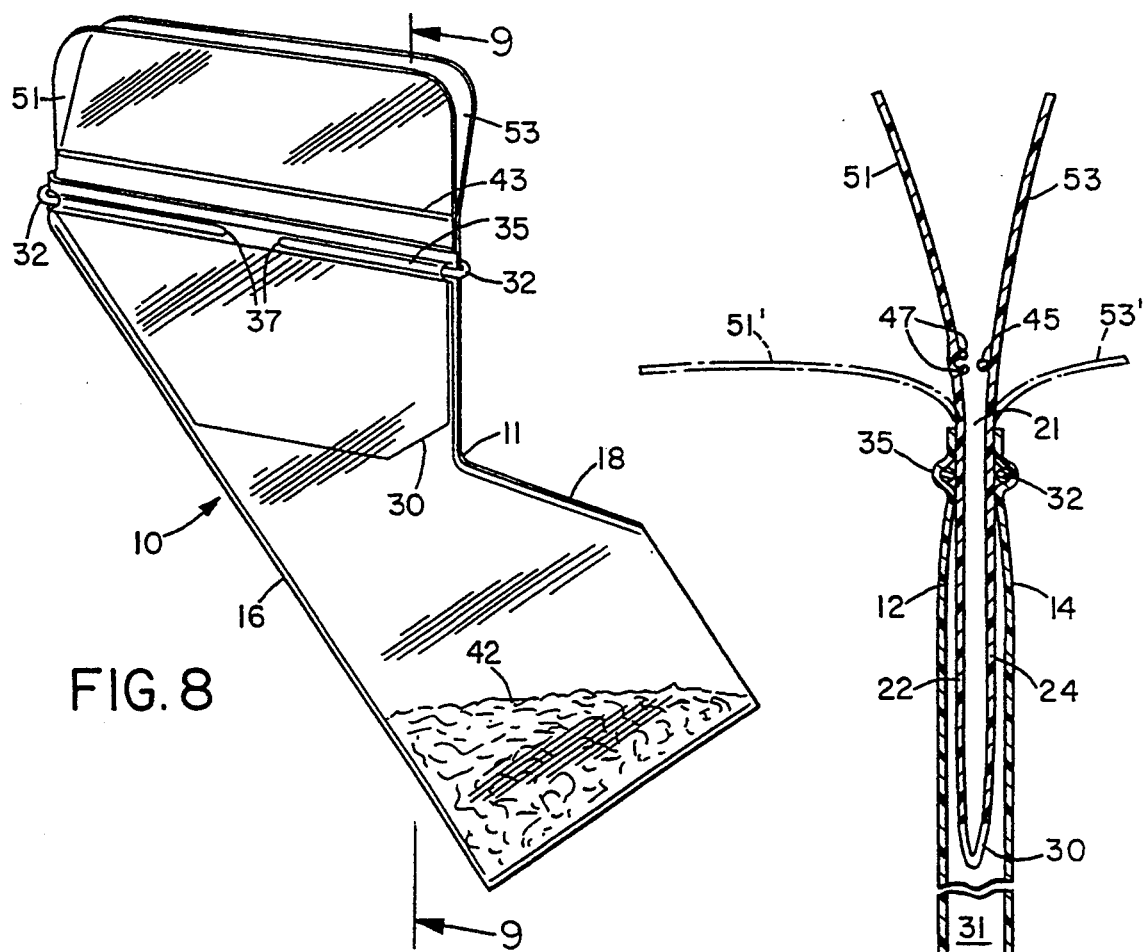
FIG. 8
FIG. 9
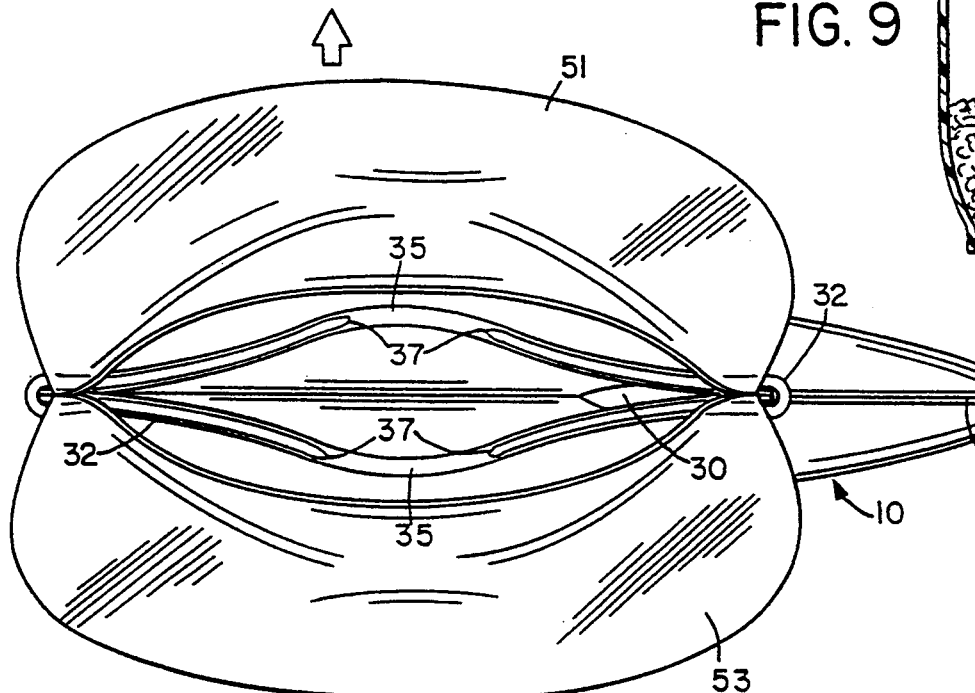
FIG. 10

FLUID CONTAINMENT BAG

CROSS-REFERENCES TO RELATED APPLICATION

This application is a divisional of application Ser. No. 07/657,354, filed Feb. 15, 1991, now U.S. Pat. No. 5,116,139, which in turn is a continuation-in-part of application Ser. No. 07/404,734, which was filed on Sep. 8, 1989 now abandoned, which in turn is a continuation-in-part of application Ser. No. 07/003,848, which was filed on Jan. 14, 1987, now abandoned.

FIELD OF THE INVENTION

The present invention relates to fluid containment bags and particularly to a disposable bag for collection of human bodily fluids such as urine, blood and vomit.

BACKGROUND OF THE INVENTION

This invention addresses the problem of providing for the collection and disposal of bodily fluid, especially waste liquids, other than with conventional bathroom, collection or sanitary facilities.

There are many situations in which a person finds himself or herself with a need to urinate but without any conventional bathroom facilities readily available. Telephone and electrical cable splicers and installers may work in underground manholes and tunnels and have no access to bathroom facilities without leaving the job site and traveling to a public restroom. Similarly, workers in the field such as telephone and electrical workers are often working at a location remote from bathroom facilities and also must stop work and travel to distant remote facilities several times a day to relieve themselves. In the past it has often been the practice that a person working in a remote or confined location would have no choice but to find a reasonably private location at the job site and urinate there. Such is a highly unsatisfactory situation, however, since it is in violation of many health and environmental regulations, particularly in more recent years when such regulations have become more prevalent.

Similarly, pilots and passengers in many types of private and military planes do not have regular bathroom facilities available to them during long flights. The problem is particularly acute in the case of military pilots who must fly long missions in extremely cramped surroundings and yet must be sufficiently alert to be able to respond instantly to hostile action.

The need for a convenient manner of safely and securely collecting and retaining waste liquids for disposal is also apparent in other situations. Those who suffer from motion sickness in vehicles such as cars and airplanes need a satisfactory container to collect and dispose of vomit which results from their motion sickness.

In a different setting, medical personnel must often dispose of significant quantities of patient' blood in surgery, trauma centers or emergency rooms where patients may be bleeding profusely. The current practice of using open containers to collect the blood has proven quite unsatisfactory.

Further, there are circumstances which do not actually involve bodily "waste" but where bodily fluid collection is performed, such as where one may wish to collect a bodily fluid for analysis or examination, as with collection of a urine or blood specimen.

There have been some previous devices which attempted to deal with the problem. The military have, for instance, been aware of the problem with respect to flight crews and the Navy and Air Force have provided flyers with a type of urine collection bag containing a sponge-like material intended to entrap the liquid. It has been found, however, that leakage of significant amounts of urine from such bags is very common, particularly when the aircraft perform aerial maneuvers.

There have also been a number of products disclosed for use by private pilots, campers, medical patients and the like, which utilized various types of containers which are intended to be sealed after use. Typical are the devices shown in U.S. Pat. Nos. 1,458,640; 3,403,715 and 4,581,763, which all involve a variety of bag and closure structures designed solely to confine urine and other body fluids in liquid form, until such contained liquids could be disposed of. As with the military bags, these products have exhibited the problems of leakage, odor, susceptibility to damage (with attendant leakage) and difficulty of storage pending disposal.

There have also been devices which incorporate means (other than the sponges mentioned above) which attempt to sequester liquid urine, such as a product previously sold commercially under the registered trademark "RESTOP." The latter product incorporates an absorbent material contained within a soluble pouch inside a conventional bag. However, the pouch takes a long time to dissolve when contacted by the urine, so that the absorbent material does not rapidly become effective. For some time after use, therefore, the "RESTOP" product is susceptible to spillage of the liquid urine, since the outer bag does not contain any closure structure capable of physical retention of the liquid urine.

There is therefore clearly a need for a convenient and practical fluid collection and containment bag which may be easily used even in a confined environment, which provides secure and complete absorption and retention of the fluids even under external forces which would otherwise tend to disperse the liquid and which can be conveniently and safely disposed of.

SUMMARY OF THE INVENTION

In its broadest form, the invention herein is a containment and disposal bag for human bodily fluids which comprises: a bag having a hollow interior defined by two sides meeting at opposite edges, a bottom and a top, with the edges and bottom sealed and the top at least partially open to receive the bodily fluids; a hydrophilic material within the bag, the material being rapidly gellable upon contact with the bodily fluids when the bodily fluids are deposited in the bag, the gellation serving to essentially completely sequester the bodily fluids and prevent the bodily fluids from thereafter being expelled from the bag; and closure means to close the top of the bag after introduction of the bodily fluids into the bag.

Preferably there are also means disposed within the bag for channeling the bodily fluids into the interior and for restricting expulsion of the bodily fluids from the interior prior to sequestration of the bodily fluids.

Preferably the hydrophilic material comprises a gellable material, commonly a polymer, which is activated upon contact with water or a water-based liquid (i.e., the bodily fluids) and which gels rapidly (normally within thirty seconds or less) to sequester the bodily fluids. More preferably, the hydrophilic material is part of a mixture of materials which also may contain enzymes, deodorants, fragrances, human body abnormality indicators and/or pregnancy indicators. The material may be in any of a variety of physical forms, such as powder, granules, fibers, mats or foam.

In its various embodiments, the bag may be rectangular or otherwise shaped to accommodate the user's needs, as for instance the L shape which is conveniently used by aircraft pilots. It may also be adapted to be worn by the user, as by being strapped to the user's leg with a catheter to the user's urinary organs, such that medical patients or incontinent persons can be ambulatory.

The rapid and complete sequestration of the bodily fluids permits the bag to be easily and conveniently used in a variety of circumstances without any possibility that the bodily fluids will become spilled or otherwise expelled from the bag, even under severe external forces such as aircraft maneuvers.

BRIEF DESCRIPTION OF THE DRAWINGS

FIG. 1 is a perspective view of a bag in accordance with the invention.

FIG. 2 is a top view of the bag of FIG. 1 in the open position.

FIG. 3 is a sectional view taken on Lines 3—3 of FIG. 1.

FIG. 4 is a partial side view showing an alternate construction of a portion of the bag.

FIG. 5 is a sectional view taken on Line 5—5 of FIG. 4.

FIG. 6 is an enlarged perspective detail view showing a closing device for the bag of FIG. 1.

FIG. 7 is a partial perspective view showing both the closure member of FIG. 6 in use and a configuration of the bag for use with a catheter.

FIG. 8 is a side view of another embodiment of the bag of the present invention, also showing an alternate means of closure of the bag.

FIG. 9 is sectional view taken on Line 9—9 of FIG. 8, also showing in phantom an alternate position.

FIG. 10 is a top view of the bag of FIG. 8 in the open position.

DESCRIPTION OF THE PREFERRED EMBODIMENTS

Figure 11:
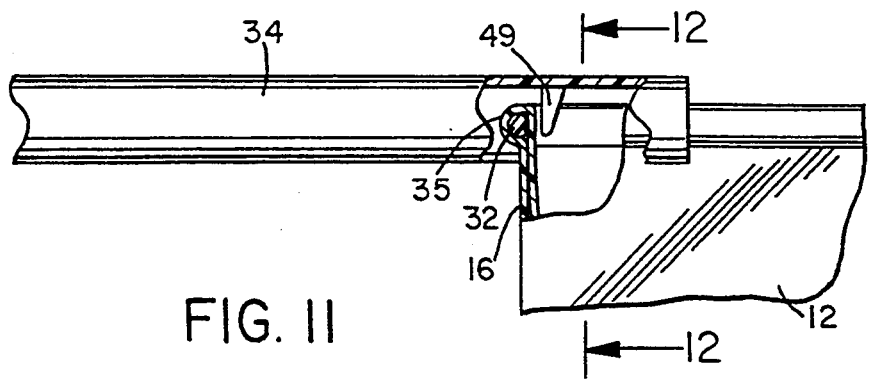
FIG. 11 is a fragmentary side view, partially in section, showing an alternate closure means of the invention.

The invention herein will be best understood by reference to the drawings, beginning with FIG. 1.

The embodiment shown in FIG. 1 is a typical embodiment of the bodily fluids disposal bag of this invention, designated, generally, by the numeral 10. This bag preferably constructed of a lightweight flexible plastic material that is impermeable and sufficiently thick and tough to resist accidental puncture under normal handling. The bag in its preferred embodiment as illustrated is a generally rectangular bag formed of a sheet of plastic or a pair of sheets of plastic, such as polyethylene, vinyl, Mylar ®, or the like. The two-sheet embodiment comprises opposing rectangular sheets 12 and 14 secured or bonded together around three peripheral edges such as by heat sealing or other form of adhesive, forming seams along side edges 16 and 18 and bottom edge 20, leaving a top opening 21 as shown in FIGS. 2 and 3. The bag may also be formed of a single sheet cut and folded such along one side and the bottom with the sides subsequently sealed to leave the top opening 21.

Figure 13:
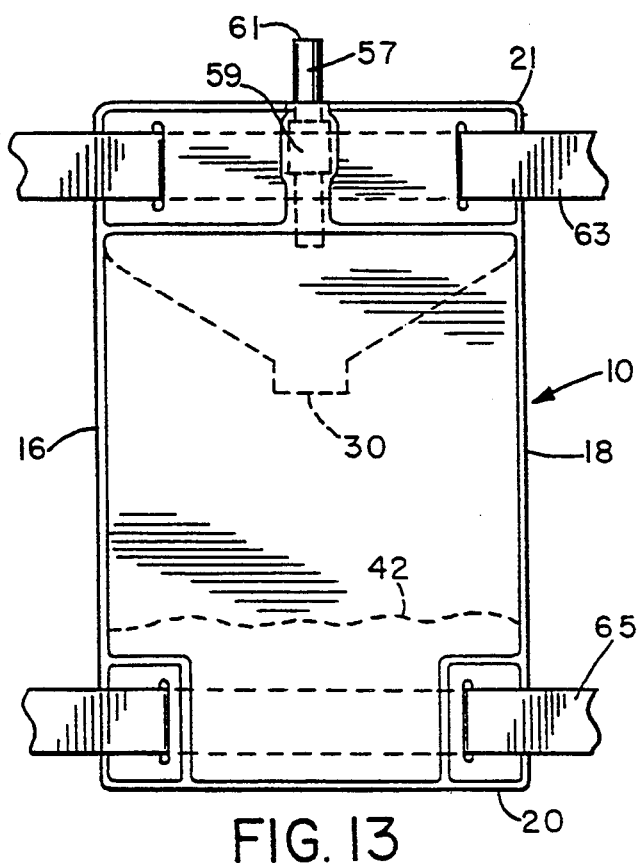
FIG. 13 is a side view of another embodiment of the bag of the present invention, particularly adapted to be strapped to the user's leg.

Disposed within the interior of the bag, as shown in FIGS. 1, 8, and 13, is a funnel comprising a pair of opposed sheets 22 and 24 connected together along seams 26 and 28 and extending downwardly from the top opening of the bag to an opening 30 that opens into the interior chamber 31 of the bag. Alternatively the funnel may be formed of a single sheet of appropriate shape folded and sealed to have a top opening 33 and a bottom opening 30. Whether a funnel is formed of separate sheets or a single sheet, the top opening 33 is coextensive with the top opening 21 of the bag.

If desired, the sheets 22 and 24 may be extensions of the side panels 12 and 14 so that the panels forming the sides and funnel are formed of a single sheet cut to the configuration of a pair of rectangular side panels 12 and 14 positioned side by side with generally triangular panels 22 and 24 extending from the top thereof. The panels are then folded alongside edges 16 and 18 and the panels 22 and 24 folded over the stiffener member 32 and the panels are heat sealed along the edges 18 and 20 below the stiffener and along the edges 26 and 28 of the panels 22 and 24.

While the lower funnel opening 30 into the interior 31 of the bag 10 is shown in FIG. 1 to be centrally located, it may be positioned at any point between sides 16 and 18. For instance, in FIG. 8 the opening 30 is at one side of the bag. Normally for general use by both males and females the opening 30 will be at the center of the bag, but embodiments of the bag designed for specific situations or to be used exclusively by one or the other of the sexes may have the opening 30 offset accordingly.

Disposed around the periphery of opening 21 at the top of bag 10 is a stiffener 32 which is generally in the form of a bow or loop. A bow, as illustrated in FIG. 2, is an elongated member made, for example, of a suitable piece of flexible plastic having sufficient memory such that when bent in the form of a bow as shown in FIG. 2, will tend to bias the top edges of the panels forming the sides of the panels outward, thus acting as a toggle and forcing the bag open. The bowed stiffener 32 also aids in support the bag. The stiffener 32 is conveniently retained in place by having the top edges of the bag be folded over to form elongated cylindrical sleeves 35 into which the stiffener 32 can be placed. For many embodiments the stiffener 32 will be sealed in place by closure of the open ends of sleeves 35 as by heat sealing. Alternatively, however, as shown in FIG. 8, the stiffener 32 may be in two separate pieces, each having a generally U shape. The two pieces are inserted respectively at opposite ends of the sleeves 35 and extend toward each other, either touching or being closely adjacent at their interior ends 37. This permits the stiffeners 32 to be removed if the user so chooses. It also permits a stiffener which may be broken to be replaced prior to use of the bag.

A convenient holding means in the form a metal eyelet or grommet 44 may be placed in an upper corner of the bag adjacent to the top to enable grasping and holding the bag while a clamp is secured thereto or while the bag is being used. The grommet 44 is securely attached to the bag and forms a firm or rigid structure for grasping.

One means of closure of the bag comprises a clamp 34 which extends along the upper opening 21 of the bag just below the upper rim formed by sleeves 35. The clamp 34 is an elongated plastic or metal tube which is formed with a slot 39 extending longitudinally for the entire length of the clamp and being defined by opposed jaws 36 and 38 for engaging and biasing the two sides of the bag together in a sealed configuration. The jaws 26 and 38 may if desired be rounded or outwardly turned, so that a smooth surface of each jaw contacts the material of the bag 10. The ends of the slot 39 are notched as shown at 40 to provide ease of sliding the clamp 34 onto the top edge of the bag 10. The clamp 34 is placed on the bag 10 by engaging an edge 16 or 18 at notch 40 just below the sleeves 35 and stiffener 32 and sliding the clamp 34 across the top of the bag 10.

Wherever possible, and particularly along the top 21, it will be desirable to have the edge seams rounded to provide comfort in use and to prevent chafing the user's skin during contact with the bag.

An alternate form the bag 10 and means of closure is shown in FIG. 8. This configuration is in the general form of an L shape with a distinct notch 11 formed in the edge 18, with the other edge 16 disposed at an angle to form the L shape. This shape of bag would be conveniently used for instance by military pilots who are restricted in their movements within the close confined spaces of the aircraft cockpit. Also shown in the configuration of FIG. 8 is an alternative form of closure of the bag which is in the form of a snap-and-seal zipper closure structure 43 formed by longitudinal rib 45 which interfits between two opposed longitudinal ribs 47 in a releasable fashion to form a seal. This type of seal, which does not require the use of clamp 34, is particularly useful in bags intended for use by persons in vehicles, particularly aircraft, for it integrates the sealing means directly into the bag structure and avoids the presence of a separate clamp. This is particularly desirable with military aircraft, where the pilot's attention should not be distracted by the need to keep track of a separate bag and clamp.

Also shown in FIGS. 8-10 is an alternate means of gripping the bag by the user which comprises adjacent extended flaps 51 and 53. These in turn are upwardly disposed extensions of sheets 22 and 24 which extend upwardly and outward of opening 21. These flaps 51 and 53 can be folded over and downward as shown in phantom in FIG. 9 (as 51' and 53' respectively). The large flaps 51 and 53 provide a large surface which may be easily grasped by users in situations where it might not otherwise be convenient or easy to hold the bag. For instance, military pilot with their hands encased in flying gloves will find these extended surfaces more easily grasped than other alternate grasping means such as grommet 44. It is also anticipated that these large surfaces may be more convenient for use by children, women or those with physical infirmities such as arthritis of the hands.

Figure 12:
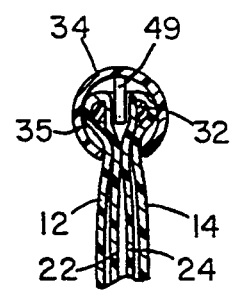
FIG. 12 is a sectional view taken on Line 12—12 of FIG. 11.

Another embodiment of clamp 34 is shown in FIGS. 11 and 12. This version of the clamp 34 includes an internal tang 49 which extends downwardly inside the hollow barrel of clamp 34 and engages the edge 16 or 18 and the outer curve of stiffener 32 when the clamp 34 is pulled to one side of the bag. This prevents the clamp from being pulled off of the bag and it also provides an effective handle in its extended position which the user may grasp during use of the bag.

A further embodiment of the bag 10 is shown in FIG. 13 in which all sides 16, 18, and 20 are sealed and top 21 is sealed across most of its extent leaving only a small opening, preferably centrally located, to accommodate tube 57 (which normally contains one-way valve 59) and which at its upper end 61 is connected to or integrated with a catheter (not shown) which extends into a person's urinary tract. The bag 10 of FIG. 13 can then be attached by means of straps 63 and 65 to the person's leg. Thus a person who is incontinent or because of surgery other medical procedures must be able to accommodate urinary drainage can still be ambulatory.

The bag preferably has a capacity to hold on the order of between ten to twenty fluid ounces (300–600 cc) of bodily fluids. This is more than adequate to accommodate the relief needs of one individual on a single occasion. The bags can of course be made larger if desired, but if made too large will be difficult for the user to handle. Smaller sizes of bags are not recommended, since they do not have sufficient volume to be adequate for a person's relief needs, except perhaps in the case of bags intended for use by infants or small children.

The bags 10 as noted above are normally made of an impervious flexible plastic material. Commonly, they will be of an opaque nature, either because of the material itself or by means of a colorant added to the plastic formulation. Alternatively, however, as shown in the configuration of FIG. 9, the bag may be made of a clear plastic so that the contents can be viewed. This would be particularly advantageous in a medical situation where a physician or other medical attendant needs to be able to observe the patient's urine for signs of abnormalities. It is also of great significance for military pilots who would need to be able to detect blood in the urine signifying internal injuries after combat. In addition, it may be convenient to have the outer sides of the bag be of a soft or otherwise comfortable feeling material for comfort in those circumstances such as with use of the bag of FIG. 13 where the user must keep the bag against his or her skin for a prolonged period.

Enclosed within the bag and critical to the function of the present invention is a quantity of an absorbent material 42 for absorbing the liquid contained within the bag. This absorbent material 42 contains a hydrophilic gellable material, usually a polymer, which is water activated and which gels very rapidly (normally within 30 seconds, and often much less than that) upon contact with a water-based liquid (such as urine or blood) and which by gelling completely absorbs and encapsulates all of the fluid. Such polymers are commercially available and are commonly found in a variety of known products, including disposable diapers and cleaning compositions. Typical examples include the acrylonitrile-based polymers described in Elias, Mega Molecules, pp. 157–158 (1987) and the acrylic polymers described in U.S. Pat. No. 4,179,367. The mixture 42 is preferably a complex mixture including not only the gellable material but also a material such as a protease enzyme to attack and break down the urine, blood or other bodily fluid to enhance the operation of the gellable material. Also included in the mixture 42 can be deodorants and fragrances. It is also possible to incorporate a biocide or antiviral material where it is expected that the bodily fluids may be contaminated as in the case of collection of blood from a surgery or medical procedure patient. The mixture 42 may by in any convenient physical form which can be placed into the bag 10;

granular, powdered, foamed, matted, woven and fibrous forms are all suitable. We have successfully used a granular material commercially available under the trade name "Sanwet IM-5600" from Hoechst Celanese, Superabsorbent Material Division, of Portsmouth, Va. which is described as containing a starch grafted sodium polyacrylate. This product is a proprietary product and the exact identification of the components and formula is not available to applicants. The product has shown the property in our tests of gelling and sequestering all bodily fluids placed into test bags within no more than twenty seconds.

The particle sizes of the granulated material can be within a fairly wide range, but preferably will have at least about 80%, more preferably 80%–90%, in the range of −40+120 mesh U.S. Sieve Series (74–240 μm). It has been found that within this range, and more preferably with at least about 50% in the range of −40+80 mesh (177–240 μm), the liquid absorbency rate is maximized. If a large proportion of the granules are smaller than 120 mesh, there will be a tendency for the material to dust unduly in handling and storage prior to use and to restrict liquid flow throughout the material during use, while if there is a large proportion with particle sizes larger than 40 mesh, the rate of liquid absorption will be slowed. A typical analysis will be 8% +40 mesh, 66% −40+80 mesh, 19% −80+120 mesh and 7% −120 mesh.

In the case of blood collection, it may be desirable to incorporate within the mixture 42 one or more testing materials which upon contact with the blood will show visible color changes indicative of specific blood disorders or the presence in the blood of specific organism. Similarly, in the case of urine collection, it is also possible to incorporate within the mixture 42 materials which with a similar color change will also indicate urinary tract infections, internal disorders which manifest signs in the urine or the presence of organisms such as bacteria or viruses in the urine. It is also contemplated to incorporate known pregnancy detectors of the type commonly used in home pregnancy test kits such that the bag when used by a female for urination, will provide an indication of whether or not the female is pregnant. Naturally, in all of these cases the bag material will be transparent so that the desired indicators can be readily observed. Also, of course, the various indicators must be compatible with the gellable absorption material and any enzyme present, so that the functions of all of the components will not be impaired by the presence of any other component.

Referring now to FIG. 4, there is illustrated a modification of the front structure of the bag 10 to accommodate it for use as an air sickness or other motion sickness bag into which the susceptible person can vomit. Such a modification could replace the existing bags currently carried on airlines and provide for easier disposal. The construction of the bag of FIG. 4 is basically the same as that of FIG. 1 with the exception that the walls of the funnel 22' and 24' are connected along seams which stop at points 46 and 48, but the sides extend downwardly forming flaps 50 and 52. These flaps each have a stiffener at edges 54 and 56 respectively extending from the edge of the seam and forcing the excess material of one flap to curl over the other flap, thus forcing the flaps to close together. This forms a self sealing one-way valve such that back breathing or inhalation of the material 42 or the expelled vomit by the person is prevented.

FIG. 7 illustrates means for adapting the bag to hospital use with a catheter. This system includes a plug 58 which has a generally teardrop shaped cross section and has a curved surface 60 for engaging and sealing to the curved portion of the opening 21 of the bag 10. The clamp 34 clamps against the plug 58 and holds it in the sealed position. The plug includes a central bore 62 through which is placed a catheter tube 64.

The bag is shown in the drawings as having a generally rectangular shape, whether straight or in the L shaped configuration. It will be evident that it may also be tapered, have a rounded or pointed bottom edge or have some other desired configuration, as long as the containment and disposal functions are adequately maintained.

The advantage of the present invention is over existing types of urine and other waste collection and disposal bags is evident. The presence of the rapidly gelling material allows for the completed collection and sequestration of the bodily fluids within a matter of seconds such that the bag of collected bodily fluids almost immediately becomes completely free of the possibility of leakage or spillage of any of the bodily fluids. Thus, the bag can be immediately closed as with the clamp 34 or the zipper closure 43 and be set aside for subsequent safe and convenient disposal. In this condition the bag is virtually impervious to accidental spillage of the contents. Thus, for instance, a pilot or airplane passenger can use the bag, seal it and within seconds set it aside with no concern that subsequent aerial maneuvers will cause any of the collected bodily fluids to be spilled within the interior of the aircraft. Similarly, a field worker can use the bag and again immediately seal it and set it aside with no concern that subsequent jostling or dropping of the bag will cause any spillage of the contents.

It will be evident that there are numerous embodiments of the present invention which, not specifically described above, are clearly within the scope and spirit of the invention. Consequently, the above description is considered to be exemplary only and the full scope of the invention is to be determined solely by the appended claims.

We claim:

1. A containment bag for bodily fluids which comprises:
 a bag having a hollow interior defined by two sides meeting at opposite edges, a bottom and a top, with said edges and bottom sealed and said top at least partially open to receive said bodily fluids;
 stiffening means aligned with and adjacent to said top of said bag for resiliently biasing said top into an opened position, said stiffening means comprising at least one flexible, resilient elongated member in contact with said bag sides adjacent said top;
 funnel means within said interior and having an open top, said funnel means being secured to said bag at said top of said bag, and extending downwardly within said interior to an open bottom for conduction of fluid entering said open top through said funnel means and into said bag, with the open bottom of said funnel being disposed intermediate between said top and bottom of said bag, said open bottom being free from attachment to said sides of said bag such that flow of fluid within said bag back toward said funnel means acts to close said funnel means to prevent escape of said fluid from said bag.

2. A bodily fluids containment bag as in claim 1 further comprising a gellable material within said bag which is activated upon contact with water or a water-based liquid and which gels rapidly to sequester said water or water-based liquid.

3. A bodily fluids containment bag as in claim 2 wherein said gellable material gels within thirty seconds of said contact with said water or water-based liquid.

4. A bodily fluids containment bag as in claim 2 wherein said gellable material is a polymer.

5. A bodily fluids containment bag as in claim 2 wherein said hydrophilic material is part of a mixture of materials which also contains at least one material selected from the group consisting of enzymes, deodorants, fragrances, human body abnormality indicators and pregnancy indicators.

6. A bodily fluids containment bag as in claim 2 wherein said hydrophilic material is in a powdered, matted, granular, fibrous, foamed, or woven physical form.

7. A bodily fluids containment bag as in claim 6 wherein said hydrophilic material is in a powdered or granular form and has at least about 80% with particle sizes in the range of −40+120 mesh U.S. Sieve Series.

8. A bodily fluids containment bag as in claim 7 wherein said hydrophilic material has about 80%–90% with particle sizes in the range of −40+120 mesh U.S. Sieve Series.

9. A bodily fluids containment bag as in claim 8 wherein said hydrophilic material also has at least about 50% with particle sizes in the range of −40+80 mesh U.S. Sieve Series.

10. A bodily fluids containment bag as in claim 1 further comprising gripping means attached to said bag for gripping of said bag by the user thereof during use.

11. A bodily fluids containment bag as in claim 10 wherein said gripping means comprises a grommet disposed in the sides of said bag.

12. A bodily fluids containment bag as in claim 10 wherein said gripping means comprises flaps extending outwardly from said top of said bag.

13. A bodily fluids containment bag as in claim 1 wherein said closure means comprises an elongated closure member which fits across said top of said bag and contains opposed jaws which contact the sides of said bag adjacent said top and bias said sides into contact to close the top opening.

14. A bodily fluids containment bag as in claim 13 wherein said elongated closure member is moveable to one side of said top of said bag to serve as a handle by which the user of said bag can grip the bag during use.

15. A bodily fluids containment bag as in claim 14 wherein said elongated closure member contains a tang on the inside thereof and projecting into the interior of said bag, said tang when said member is moved to one side of said top contacting the inside edge of the top opening of said bag and preventing said member from becoming disengaged from said bag.

16. A bodily fluids containment bag as in claim 1 wherein said closure means comprises cooperating ribs on the inside surfaces of the sides of said bag adjacent, which ribs interfit to close the top opening of said bag.

17. A bodily fluids containment bag as in claim 1 wherein said bag further comprises means for attachment to the body or limb of a user and conduit means comprising a catheter adapted for enabling said user to use said bag for urine collection while said user is ambulatory.

18. A bodily fluids containment bag as in claim 1 wherein said funnel means has its bottom opening in the form of a self sealing one-way valve.

19. A bodily fluids containment bag as in claim 1 wherein said bag has the form of an L shape.

20. A containment bag as in claim 1 wherein said funnel means includes edges which converge toward said open bottom.

21. A containment and disposal bag for bodily fluids which comprises:
a bag having a hollow interior defined by two sides meeting at opposite edges, a bottom and a top, with said edges and bottom sealed and said top at least partially open to receive said bodily fluids;
funnel means within said interior and having an open top, said funnel means being secured to said bag at said top of said bag, and extending downwardly within said interior to an open bottom for conduction of fluid entering said open top through said funnel means and into said bag, with the open bottom of said funnel being disposed intermediate between said top and bottom of said bag, said open bottom being free from attachment to said sides of said bag such that flow of fluid within said bag back toward said funnel means acts to close said funnel means to prevent escape of said fluid from said bag;
stiffening means aligned with and adjacent to said top of said bag for resiliently biasing said top into an opened position, said stiffening means comprising at least one flexible, resilient elongated member in contact with said bag sides adjacent said top; and
closure means for closing the top of said bag after introduction of said bodily fluids into said bag.

22. A bodily fluids containment bag as in claim 21 wherein said stiffening means are removably attached to said bag adjacent said top.

23. A bodily fluids containment bag as in claim 22 wherein said stiffening means are removably sheathed in sleeves disposed adjacent said top of said bag.

24. A bodily fluids containment bag as in claim 23 wherein said sleeves are formed in said sides of said bag.

25. A bodily fluids containment bag as in claim 22 wherein said stiffening means comprises a plurality of elongated members which cooperate to bias said top into an opened position.

26. A bodily fluids containment bag as in claim 4 wherein said stiffening means comprises a bow shaped member which can be manually bowed outward by the user of said bag to bias said top opening into an opened position.

27. A bodily fluids containment bag as in claim 26 wherein said bow shaped member acts as a toggle to hold said top in said opened position until said member is manually moved to bias said top into a substantially closed position.

28. A bodily fluids containment bag as in claim 21 wherein said stiffening means comprises a plurality of elongated members which cooperate to bias said top into an opened position.

29. A containment bag as in claim 21 wherein said funnel means includes edges which converge toward said open bottom.

30. A containment bag for bodily fluids which comprises:
a bag having a hollow interior defined by two sides meeting at opposite edges, a bottom and a top, with said edges and bottom sealed and said top at least partially open to receive said bodily fluids;

a gellable hydrophilic material within said bag, said material becoming fully gelled within thirty seconds of said contact with said bodily fluids when said bodily fluids are deposited in said bag, said gellation serving to essentially completely sequester said bodily fluids and prevent said bodily fluids from thereafter being expelled from said bag;

funnel means within said interior and having an open top, said funnel means being secured to said bag at said top of said bag, and extending downwardly within said interior to an open bottom for conduction of fluid entering said open top through said funnel means and into said bag, with the open bottom of said funnel being disposed intermediate between said top and bottom of said bag, said open bottom being free from attachment to said sides of said bag such that flow of fluid within said bag back toward said funnel means acts to close said funnel means to prevent escape of said fluid from said bag.

31. A bodily fluids containment bag as in claim 30 wherein said gellable material is a polymer.

32. A bodily fluids containment bag as in claim 30 wherein said hydrophilic material is part of a mixture of materials which also contains at least one material selected from the group consisting of enzymes, deodorants, fragrances, human body abnormality indicators and pregnancy indicators.

33. A bodily fluids containment bag as in claim 30 wherein said hydrophilic material is in a form selected from the group consisting of powdered, matted, granular, fibrous, foamed, and woven physical forms.

34. A bodily fluids containment bag as in claim 33 wherein said hydrophilic material is in a powdered or granular form and has at least about 80% with particle sizes in the range of −40+120 mesh U.S. Sieve Series.

35. A bodily fluids containment bag as in claim 34 wherein said hydrophilic material has about 80%–90% with particle sizes in the range of −40+120 mesh U.S. Sieve Series.

36. A bodily fluids containment bag as in claim 35 wherein said hydrophilic material also has at least about 50% with particle sizes in the range of −40+80 mesh U.S. Sieve Series.

37. A bodily fluids containment bag as in claim 20 wherein said bag further comprises means for attachment to the body or limb of a user, and said channel means comprises a catheter adapted for enabling said user to use said bag for urine collection while said user is ambulatory.

38. A containment bag for bodily fluids which comprises:

a bag having a hollow interior defined by two sides meeting at opposite edges, a bottom and a top, with said edges and bottom sealed and said top at least partially open to receive said bodily fluids;

channel means at least partially within said interior and secured to said bag at said top of said bag, and extending downwardly within said interior and terminating in one-way valve means for conduction of bodily fluid entering through said channel means and into said bag, with said one-way valve means being disposed intermediate between said top and bottom of said bag and free from attachment to said sides of said bag such that flow of fluid within said bag back toward said channel means acts to close said one-way valve means to prevent escape of said fluid from said bag; and closure means for closing the top of said bag after introduction of said bodily fluids into said bag, said closure means comprising an elongated cylindrical closure member having a longitudinal slot which fits across said top of said bag, said longitudinal slot defining opposed jaws for contacting the sides of said bag adjacent said top and biasing said sides into contact to close the top opening.

39. A bodily fluids containment bag as in claim 38 further comprising gripping means attached to said bag for gripping of said bag by the user thereof during use.

40. A bodily fluids containment bag as in claim 39 wherein said gripping means comprises a grommet disposed in the sides of said bag.

41. A bodily fluids containment bag as in claim 39 wherein said gripping means comprises flaps extending outwardly from said top of said bag.

42. A bodily fluids containment bag as in claim 38 wherein said elongated closure member is moveable to one side of said top of said bag to serve as a handle by which the user of said bag can grip the bag during use.

43. A bodily fluids containment bag as in claim 42 wherein said elongated closure member contains a tang on the inside thereof and projecting into the interior of said bag, said tang when said member is moved to one side of said top contacting the inside edge of the top opening of said bag and preventing said member from becoming disengaged from said bag.

44. A bodily fluids containment bag comprising:

a hollow interior defined by two sides meeting at opposite edges, a bottom and a top, with said edges and bottom sealed and said top at least partially open to receive said bodily fluids;

channel means at least partially within said interior and secured to said bag at said top of said bag, and extending downwardly within said interior and terminating in one-way valve means for conduction of bodily fluid entering through said channel means and into said bag, with said one-way valve means being disposed intermediate between said top and bottom of said bag and free from attachment to said sides of said bag such that flow of fluid within said bag back toward said channel means acts to close said one-way valve means to prevent escape of said fluid from said bag; and closure means for closing the top of said bag after introduction of said bodily fluids into said bag, said closure means comprising cooperating ribs on the inside surfaces of the sides of said bag adjacent one another, which ribs interlock to hold said top opening of said bag in a closed position.

45. A bodily fluids containment bag as in claim 38 wherein said bag has the form of an L shape.

46. A containment and disposal bag for bodily fluids which comprises:

a bag having a hollow interior defined by two sides meeting at opposite edges, a bottom and a top, with said edges and bottom sealed and said top at least partially open to receive said bodily fluids;

channel means at least partially within said interior and secured to said bag at said top of said bag, and extending downwardly within said interior and terminating in one-way valve means for conduction of bodily fluid entering through said channel means and into said bag, with said one-way valve means being disposed intermediate between said top and bottom of said bag and free from attachment to said sides of said bag such that flow of fluid within said bag back toward said channel means acts to close said one-way valve means to prevent escape of said fluid from said bag;

stiffening means aligned with and adjacent to said top of said bag for resiliently biasing said top into an opened position, said stiffening means comprising at least one flexible, resilient elongated member in contact with said bag sides adjacent said top; and closure means for closing the top of said bag after introduction of said bodily fluids into said bag, said closure means comprising opposed ribs on the in side surfaces of the sides of said bag that interlock to hold said top in a closed position.

47. A bodily fluids containment bag as in claim 46 wherein said stiffening means are removably attached to said bag adjacent said top.

48. A bodily fluids containment bag as in claim 46 wherein said stiffening means are removable sheathed in sleeves disposed adjacent said top of said bag.

49. A bodily fluids containment bag as in claim 48 wherein said sleeves are formed in said sides of said bag.

* * * * *